US008647304B2

(12) United States Patent
Axelsson et al.

(10) Patent No.: US 8,647,304 B2
(45) Date of Patent: Feb. 11, 2014

(54) IMPLANT AND METHOD FOR ITS MANUFACTURE

(75) Inventors: Robert Axelsson, Gränna (SE); Martin Johansson, Vallda (SE); Anette Johnsson, Jönköping (SE); Bjørn Edwin, Sætre (NO); Erik Fosse, Oslo (NO)

(73) Assignee: Ostomycure AS, Oslo (NO)

( * ) Notice: Subject to any disclaimer, the term of this patent is extended or adjusted under 35 U.S.C. 154(b) by 737 days.

(21) Appl. No.: 12/280,610

(22) PCT Filed: Feb. 28, 2007

(86) PCT No.: PCT/IB2007/050646
§ 371 (c)(1),
(2), (4) Date: Oct. 29, 2008

(87) PCT Pub. No.: WO2007/099500
PCT Pub. Date: Sep. 7, 2007

(65) Prior Publication Data
US 2009/0192464 A1 Jul. 30, 2009

(30) Foreign Application Priority Data

Feb. 28, 2006 (EP) ..................................... 06110490

(51) Int. Cl.
*A61M 5/178* (2006.01)
(52) U.S. Cl.
USPC .................................................. 604/164.04
(58) Field of Classification Search
USPC .......... 604/164.04, 288.01–288.04, 175, 337, 604/338
See application file for complete search history.

(56) References Cited

U.S. PATENT DOCUMENTS

| 3,663,965 | A |   | 5/1972  | Lee, Jr. et al. ............... 623/23.64 |
| 4,119,100 | A |   | 10/1978 | Rickett .................... 604/103.03 |
| 4,183,357 | A |   | 1/1980  | Bentley et al. |
| 4,217,664 | A |   | 8/1980  | Faso ...................................... 3/1 |
| 5,098,397 | A | * | 3/1992  | Svensson et al. ............. 604/175 |

(Continued)

FOREIGN PATENT DOCUMENTS

| EP | 477 475 A2 | 4/1992 |
| EP | 1 632 201 A1 | 3/2006 |

(Continued)

OTHER PUBLICATIONS

Machine Translation of description of WO2005056079A1 to Skiera, et al. Translated by http://ep.espacenet.com/ on Feb. 23, 2011.*

(Continued)

*Primary Examiner* — Nicholas Lucchesi
*Assistant Examiner* — Melissa A Snyder
(74) *Attorney, Agent, or Firm* — Winston & Strawn LLP

(57) ABSTRACT

An implant for percutaneous implantation through the abdominal wall for encircling and engaging an externalized length of a body duct of a human or animal patient. The implant has an exterior ring section protruding outwardly from the abdominal wall with a free end which serves for mounting of a detachable device, and an interior section extending through the abdominal wall and inside the patient for internal fixation of the implant. The exterior ring section and interior section have a common axis. The internal circumference of at least a part of the exterior ring section above the interior section is arranged with a biocompatible, integrated ingrowth means for the exterior surface of the body duct wall.

34 Claims, 8 Drawing Sheets

(56) References Cited

U.S. PATENT DOCUMENTS

| | | | |
|---|---|---|---|
| 5,423,761 A | 6/1995 | Hein et al. | 604/167.01 |
| 5,425,761 A | 6/1995 | Lundgren | 623/11 |
| 5,882,341 A * | 3/1999 | Bousquet | 604/175 |
| 6,017,355 A | 1/2000 | Hessel et al. | 606/184 |
| 6,438,397 B1 * | 8/2002 | Bosquet et al. | 600/310 |
| 7,935,096 B2 | 5/2011 | Johansson et al. | 604/338 |
| 2001/0051794 A1 * | 12/2001 | Bestetti et al. | 604/288.04 |
| 2002/0099344 A1 * | 7/2002 | Hessel et al. | 604/338 |
| 2004/0006396 A1 * | 1/2004 | Ricci et al. | 623/32 |
| 2006/0052759 A1 | 3/2006 | Johansson et al. | 604/277 |
| 2011/0178540 A1 | 7/2011 | Axelsson et al. | 606/153 |
| 2011/0196324 A1 | 8/2011 | Johansson et al. | 604/338 |
| 2012/0123361 A1 | 5/2012 | Johansson et al. | 604/337 |

FOREIGN PATENT DOCUMENTS

| | | |
|---|---|---|
| EP | 1633201 | 8/2006 |
| GB | 2 045 084 A | 10/1980 |
| GB | 2 105 197 A | 3/1983 |
| JP | 2002507901 A | 3/2002 |
| WO | WO98/58691 | 12/1998 |
| WO | WO 00/62722 | 10/2000 |
| WO | WO 01/08597 A1 | 2/2001 |
| WO | WO 2005056079 A1 * | 6/2005 |
| WO | WO 2007/099500 A1 | 9/2007 |

OTHER PUBLICATIONS

International Search Report and Written Opinion PCT/IB32007/050646.

International Search Report and Written Opinion PCT/IB2007/050646.

European Search Report, Appl. No. EP 07114671, Dec. 4, 2007.

International Search Report, Appl. No. PCT/EP2008/060837, Nov. 7, 2008.

U.S. Appl. No. 12/674,666, filed Apr. 11, 2011.

U.S. Appl. No. 12/674,666, Non-Final Office Action, Jan. 18, 2013.

* cited by examiner

IMPLANT AND METHOD FOR ITS MANUFACTURE

This application is a 371 filing of International Patent Application PCT/IB2007/050646 filed Feb. 28, 2007.

BACKGROUND

The invention relates to an implant for percutaneous implantation through the abdominal wall for encircling and engaging an externalised length of a body duct of a human or animal patient, said implant is of the kind comprising an exterior ring section at least a part of which is protruding outwardly from the abdominal wall with a free end which serves for mounting of a detachable device, and an interior section extending through the abdominal wall and inside the patient for internal fixation of the implant, and the exterior ring section and the interior section have a common axis.

A method for manufacturing the implant according to the present invention is also provided.

A method for implantation of the implant according to the present invention into an animal or a human body is also described together with preferred uses.

Many diseases such as e.g Crohn's disease, ulcerative colitis, intestinal cancer and adenomatous polyposis or bladder cancer require removal of all or part of the intestines or bladder. When the intestines or the bladder are removed, the bodily wastes are expelled through a new surgical opening in the abdominal wall. The surgery to create the new opening, the stoma, is called ostomy. The main steps in the surgery are to create an abdominal opening, externalise the relevant body duct through the abdominal wall and skin, and suture the body duct to the skin so as to complete the stoma. Most persons with ostomies must wear special appliances over the stoma and use ostomy pouches to collect and eliminate waste. A detailed discussion of various diseases and conventional and novel surgical procedures involving ostomy are found in the applicant's own European patent application EP 04077475.4, published as EP 1632201.

Drawbacks such as ulceration, incisional hernia, or bulging of the bowel through the incision, narrowing of the stoma, scar tissue and bowel obstruction, avulsion, skin irritation from stool that leaks under the drainage bag and necrosis are often seen in the conventional procedures described in European patent application EP 04077475.4, published as EP 1632201.

U.S. patent application Ser. No. US 2002/0099344 discloses an implant for surrounding an already existing ostomy or for surrounding a newly performed ordinary ostomy. The implant has a smooth inner side and an internal periphery which is substantially greater than the external periphery of the ostomy in order to obtain a desired essential distance to the implant wall and avoid any contact between intestine and implant. This known implant is neither designed for nor intended for fixation of the intestine.

U.S. Pat. No. 6,017,355 disclose another implant based on the same structural and functional design. An annular separation of between 5 to 25 mm between the externalised body duct and the implant is typical. The exterior and interior circumference of the part of the implant inserted through the abdominal wall has a tight-fitting textile surface coating suitable for growing together with the external skin tissue on both annular implant sides. This known implant is neither designed for nor intended for fixation of the intestine to the implant.

Many of the above mentioned drawbacks are remedied with the implant according to the above referred European patent application EP 04077475.4, published as EP 1632201. This known implant has a tubular part with a perforated flange extending radially from the bottom of the tubular part. Implantation is based on a novel surgical implantation technique, in which the perforated flange is placed directly on the fascia above the intestinal serosa and secured by means of e.g sutures. Superficial lesions on opposing surfaces of the intestinal wall and the peritoneum enhances natural tendency to create adherences and the growing together of fascia, peritoneum and the intestine below the implant. Optionally, a soft mesh on the bottom of the implant is used to promote healing. The design of the flange according to European patent application EP 04077475.4, published as EP 1632201 is incorporated in the present application by reference as a preferred embodiment of a suitable flange.

A tubular implant with a flange protruding from the proximal end is known from U.S. Pat. No. 4,217,664. This implant is used as a permanent, closeable stoma and includes a flexible, pliable sleeve of biocompatible, soft, mesh material, e.g. polypropylene. One end of the sleeve is split into two split parts. One split part is attached, e.g. by heat sealing, to the inside of the tubular part close to the flange to engage the serosa of a short end part of a body duct externalised through the implant. The other split part is arranged outside the implant. The opposite free end of the sleeve extends through the abdominal wall and ends in a patch secured to the inner side of the parietal peritoneum. Since a flexible sleeve can move in response to the peristaltic movements of the externalised intestine there is a great risk that the connection of the tissue growing into the sleeve is too weak at the beginning of the healing process to resist peristaltic movement. The fragile tissue bond may rupture in response to movement of the sleeve during peristaltic and in response to passage of substance. This prevents fast healing and protracts patient recovery. Attachment of serosa to the smooth internal diameter of the implant via the mesh does not occur and the implant according to U.S. Pat. No. 4,217,664 do not have a large attachment to the implant itself.

Still there is a strong need for improved implants for ostomies to meet the needs of the large number of patient's requiring ostomy.

SUMMARY OF THE INVENTION

In a first aspect according to the present invention, a percutaneous implant of the kind mentioned in the opening paragraph is provided, which can be used in ostomy for externalisation of a body duct, such as an intestine, through the abdominal wall.

In a second aspect according to the invention, an implant is provided, which provides a leak-proofed stable, effective and well vascularised skin-implant junction.

In a third aspect the invention provides an implant, which allows for generation of at tissue bond, which can resist mechanical stress in both radial and axial directions.

In a fourth aspect according to the invention, an implant is provided which can be detachably attached to and disconnected from devices, such as e.g. caps, pouches or catheters, thereby giving the surgically treated patient an unprecedented comfort.

In a fifth aspect according to the invention an implant is provided which causes an unprecedented minimal allergic and inflammatory reaction.

The novel and unique features, whereby this is achieved according to the present invention, is the fact that the internal circumference of at least a part of the exterior ring section above the interior section is arranged with a biocompatible, integrated ingrowth means for the exterior surface of the body duct wall.

During the surgical implantation procedure an opening is made at a relevant site through the abdominal wall. The implant is located in the abdominal opening with the exterior section protruding from the patient. A part of the interior section is designed for being situated on the lower or upper fascia, however within the scope of the present invention this part of the interior section can be situated on any of the tissue layers of the internal abdominal wall, and if required secured in situ e.g. by suturing or stapling. This suturing is optionally.

The body duct, e.g. the colon, is then externalised through the internal diameter of the implant so that the interior section carefully encircles, guides and supports the externalised body duct. The outmost tissue layer, e.g. the serosa or any other exposed layer of the body duct's exterior wall is thereby brought into engaging contact with the ingrowth means to trigger the gradual ingrowth of tissue, generation of connective tissue and firm integration of body wall, intestine and implant. This position of the externalised body duct inside the implant may initially be secured using appropriate mechanical means, such as sutures or a stent to keep ingrowth means and body duct in intimate contact to support the integration process.

The biocompatible, integrated ingrowth means of the internal circumference of at least a part of the exterior ring section above the interior section serves for ingrowth of the wall of the body duct. The outermost part of the exterior ring section may for some uses be left free of ingrowth means to prevent the mucous membrane of the body duct from surrounding the protruding free edge of the exterior ring section. This ensures a clean, tissue free platform for attachment of a detachable device, such as a cap, a pouch or a catheter.

In a preferred embodiment the interior section comprises an intermediate section emerging from the exterior ring, said intermediate section is optionally axially divided into a first intermediate section part and a second intermediate section part emerging from the first intermediate section part, said interior section extends into an anchoring section, said second intermediate or said intermediate section part comprises circumferentially spaced apart first connection members connecting the second intermediate section part or the intermediate section with the anchoring section.

Abdominal tissue infiltrates the first connection members and spreads into contiguity with serosal tissue and any other accessible tissue, which has infiltrated the ingrowth means due to the intimate contact with said ingrowth means. The tissues generated in this manner subsequently grow together to generate a vascularised, coherent tissue attachment between body duct, implant and abdominal tissue. This tissue attachment is strong, reliable and has a tensile strength of a size that even shortly after surgery eliminates the risk of rupturing upon manipulation of the implant during daily care. Also, the anchoring section ends up infiltrated with or enclosed by vascularised connective tissue irrespective of whether or not the anchoring section has been pre-secured using mechanical means.

In a preferred embodiment at least the radial, circumferential spaces between the first connection members of the intermediate section or the second intermediate section part is also provided with integrated ingrowth means along the internal circumference. This embodiment provides the possibility of also allowing ingrowth of body duct tissue, e.g. serosa, to the interior wall of any of the intermediate sections, and generation of connective tissue to perfect integration, backing and fixation of the body duct to the implant, and as a result also to the surgical abdominal site. A further advantage of this embodiment is that the ingrowth means prevents one or more areas or regions of the externalised body duct from escaping through any open spaces between the first connections members with the risk that these areas or regions is squeezed or strangulated and becomes necrotic. Also, the risk of fistulation and hernia is substantially reduced or even eliminated.

In a modification of this preferred embodiment the entire internal circumference of any of the first and second intermediate section parts or the intermediate section are provided with integrated ingrowth means for the exterior surface of the body duct, so that also the surface of the first connections members facing the body duct is provided with ingrowth means.

As mentioned above, prior art ingrowth means are flexible meshes, which adapt to the different environmental conditions. This means that the flexible meshes is able to enter small pockets, cavities or outpouchings in the artificial abdominal wall opening or to close around or grow together with an adjacent area of the body duct. Use of flexible meshes in externalising body ducts surgery may involve e.g. the risk of duct obstruction if the duct walls gets too close to each other, e.g. if the abdomen swells or the duct walls accidentally engage and cohere. Another risk is that the sleeve promotes encapsulation or sheathing of body duct content in the natural or artificially made pockets. Subsequent microbiological growth, gas formation within the pocket, inflammation or simply chemical attacks may result in severe tissue damage. The present invention overcomes a prejudice within the art of using implants with rigid ingrowth means to assist externalisation of body ducts.

It has contrary to the previous teachings been demonstrated, that rigid ingrowth means of e.g. biologically, acceptable titanium willingly grows together with serosa to create a coherent well-vascularised structure. This finding is highly unexpected.

The integrated ingrowth means has a plurality of passageways or channels that provide for ingrowth of the exterior surface of the body duct wall, e.g ingrowth of the serosa. The passageways or channels are sized in dependency of the kind of body duct to be externalized and on the basis of surgical experience. However it is important that the sizes, diameters and cross-sectional dimensions of the passageways, channels, or cavities throughout the ingrowth means are selected to allow generation of vascularised new tissue so that nutrition and medication easily can be supplied to the new tissue.

The integrated ingrowth means may advantageously be configured as a netting, mesh, maze or sponge having openings, cavities, channels or any other kind of passageways that allows ingrowing tissue to infiltrate the ingrowth means and optionally penetrating said ingrowth means wherever it is appropriate to create the required strong attachment between implant, abdominal wall and body duct wall.

Preferred cross-sectional shapes of any of the plurality of passageways or channels or openings in a netting or mesh are polygonal cross-sections, preferably hexagonal cross-sections.

In a preferred embodiment a recess is provided along the internal circumference of the exterior ring section above the interior section, whereby the recess provides a circumferential gap between the exterior surface of the ingrowth means and the opposing surface of the wall of the recess. This gap serves as an escape route or reservoir for new tissue generated at the free end of the externalised body duct and assists to prevent the mucosa from getting around the outermost edge of the exterior ring section. Furthermore, the ingrowth to the recess prevents the free end of the exterior ring section from becoming stenotic. It is important when used with a detachable device that the outer surface of the exterior ring section is kept free of tissue since a detachable device otherwise cannot be attached leak-proofed to the implant.

A firm and reliable attachment of the implant inside the body can be obtained if the implant has an anchoring section extending radially from the intermediate section or the second intermediate section part opposite the exterior ring section. The radial extent of the anchoring section provides an increased support surface, and increased exposed attachment and tissue integration and ingrowth surface. Further, this firm fixation of the implant reduces the relative movement between implant and tissue thereby keeping the tissue reaction to a minimum.

In a preferred embodiment the anchoring section is conic to better conform to the overall curvature of the internal application site and to prevent local pressure due to for example tilting either after implantation or caused by accidental mechanical forces. Any suitable degree of conicity is foreseen within the scope of the present invention and the degree of conicity may be chosen according to the patients specific anatomic conditions to provide each patient with the most comfortable and appropriate relief.

In an alternative embodiment according to the present invention the anchoring section may comprise an inner anchoring ring extending from the intermediate section or the second intermediate section part, an outer anchoring ring, and at least one second connection member for connecting the inner anchoring ring with the outer anchoring ring. The outer anchoring ring advantageously has a greater diameter than the inner anchoring and is concentric with said inner anchoring ring. This simple embodiment may be made flat or conic according to the surgical requirements, e.g. the specific anatomic conditions prevailing at the surgical site.

Various modification of the anchoring section is available within the scope of the present invention.

For example the anchoring section can be made so that a first connection point between a first end of the at least one second connection member and the inner anchoring ring is angularly offset with an angle from a second connection point between a second end of the second connection member and the outer anchoring ring. Such an anchoring section design is very easy for the surgeon to suture to the surrounding tissue, and provide the anchoring section with flexibility and resiliency between the inner anchoring ring and the outer anchoring ring, i.e. in the anchoring section plane.

In yet another exemplary embodiment of the anchoring section of an implant according to the present invention the outer anchoring ring is constituted of spaced apart substantially semicircular segments. This design could be the choice of the surgeon in case the subjacent supporting tissue on which the anchoring section rests, in the implanted state of use, is more or less dome-shaped because the spacing of the segments also provide for annular flexibility.

The attachment and connection between tissue and implant are important and it is preferred that at least one of the following components of the implant is provided with through-going transverse openings, said component being one or more first connection members, the inner anchoring ring, the outer anchoring ring or the at least one second connection member. Any of these through-going transverse openings can, in addition to allow ingrowth of tissue and vascularisation, be used for suturing or stapling of the implant firmly to its surroundings, including the body duct.

The exterior face of the interior section may in certain embodiments further comprise annular projections for further securing the implant to the adjacent body wall tissue and may if desired be given a surface topography promoting tissue attachment.

For some externalised body ducts it may be preferred that the implant is modified in that any of the intermediate section or its parts are made entirely as an integrated ingrowth means, preferably in the form of netting, mesh, maze or sponge, or as one or more concentric structures of these.

The surgeon may decide during surgery or in advance which configuration of implant that suits the patient best. However, the appropriate implant may have ingrowth means with a radial thickness equal to or smaller than the wall thickness of the body duct. Such data is easily determined by experimentation and tabularized or otherwise stored for the convenience of the surgeon and subsequent surgical procedure.

The preferred method for manufacturing an implant comprises providing a first tubular blank for the manufacture of the exterior section, and at least the first intermediate section of the interior section and optionally the second intermediate section part, providing a second tubular blank for the manufacture of the ingrowth means, providing a third blank, at least a part of which is disc-shaped, for the manufacture of the anchoring section and the second intermediate section part if this section not is provided in the first blank, finish machining the shapes of the blanks using turning and cutting, and drilling or otherwise providing any space, window, and/or through-going opening of the exterior and the interior section, and deburring and polishing at least the exterior section. Then the channels or passageways of the ingrowth means are made by laser cutting, subsequently assembling by laser welding any of the interior section, first intermediate section part or second intermediate sections part as provided, to the anchoring section, to a intermediate unit, rounding any selected edges of the intermediate unit and the ingrowth means, preferably by tumbling and/or electropolishing, blasting any selected tissue contacting part of any of the intermediate unit and/or the ingrowth means, and finally laser welding the intermediate unit and the ingrowth means together to provide the implant.

Nearly any design of ingrowth means can be made using the laser cutting technology, because laser cutting takes direct input of electronic data from a CAD drawing. Typically, a laser cut hole tapers in the exit direction of the cutting beam and cut edges are void of burrs.

Preferably the implant is subjected to a finish blasting to provide the optimum surface topography for any ingrowing tissue and tissue adjacent a surface of the implant.

BRIEF DESCRIPTION OF THE DRAWINGS

Examples of embodiments of the implant according to the invention is described below in more details with reference to the Examples and the drawing, in which.

DETAILED DESCRIPTION OF THE PREFERRED EMBODIMENTS

Figure 1:
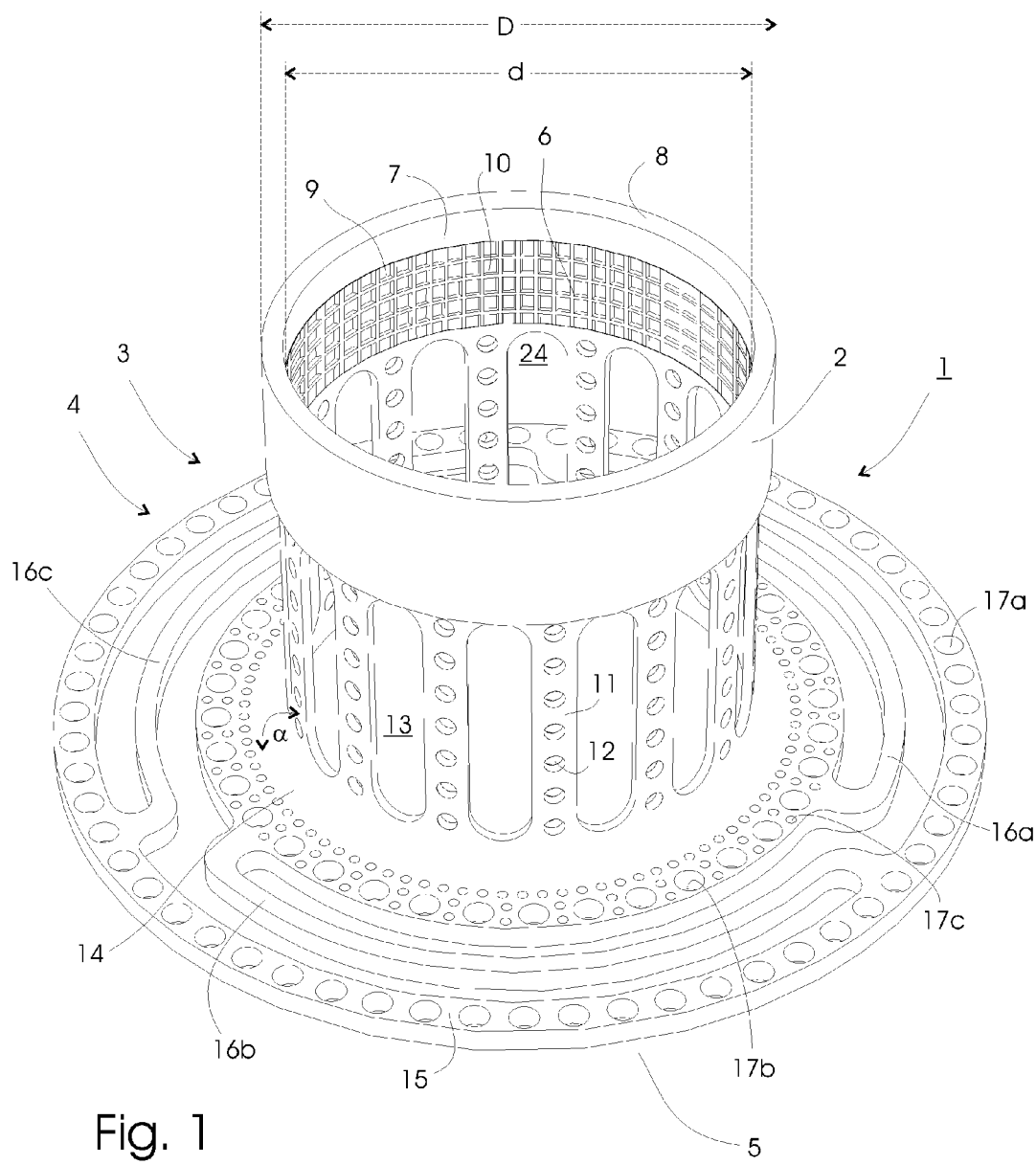
FIG. 1 shows a perspective view of a first embodiment of an implant according to the present invention.

The implant shown in FIG. 1 is in its entirety designated with reference number 1 and will be described in relation to an intestine only by way of example, however the use with any other body duct is intended within the scope of the present invention.

FIG. 1 shows a substantially tubular implant 1 with an axial exterior ring section 2, an axial interior section 3, consisting of an intermediate section 4 and an anchoring section 5, which extends radially from the end of the intermediate section 4 opposite the exterior ring section 2 in an angle α of approximately 90°.

Adjacent the intermediate section 4 along the internal diameter of the exterior ring section 2, said exterior ring section 2 is provided with an ingrowth means 6. In this embodiment the axial height of the ingrowth means 6 is smaller than the axial height of the exterior ring section 2 to leave a rim portion 7 and outermost edge 8 free of tissue. The ingrowth means 6 is shown as a netting 9 having apertures 10. Is should be noted that the size of the apertures in the netting or any other ingrowth means is illustrated by way of example only, and that smaller or larger apertures or channels often may be preferred. The main criteria for selecting the size of the aperture of the ingrowth means is that vascularised tissue can be generated, so that pathological conditions can be treated orally, and vital and viable tissue surrounds the implant.

In the case show, the intermediate section has in total twelve equally circumferential spaced apart first connection members 11 between the exterior ring section 2 and the anchoring section 5. Two first connections members 11 define a space or window 13 in-between them. Each first connection member 11 is a thin flat rod 11 with transverse through-going openings 12. However, other structures of first connection members may be quite as usable, for example first connection members of rigid thread formed into zig-zag-shaped structure.

The anchoring section 5 consists of an inner anchoring ring 14, an outer anchoring ring 15 concentric with the inner anchoring ring 14 and three elongated connection members 16a, 16b, 16c for connecting the inner anchoring ring 14 with the outer anchoring ring 15. The anchoring section 5 is shown with a plurality of ingrowth and/or securing holes 17a, 17c, 17c. For further description of the details of the anchoring ring references are made to European patent application EP 04077475.4, published as EP 1632201 and this description is incorporated by reference in the present application.

In the embodiment shown in FIG. 1 the exterior ring section 2 has an outer diameter D greater than the outer diameter d of the intermediate section 4. This diameter difference allows space for abdominal tissue ingrowth.

Figure 2:
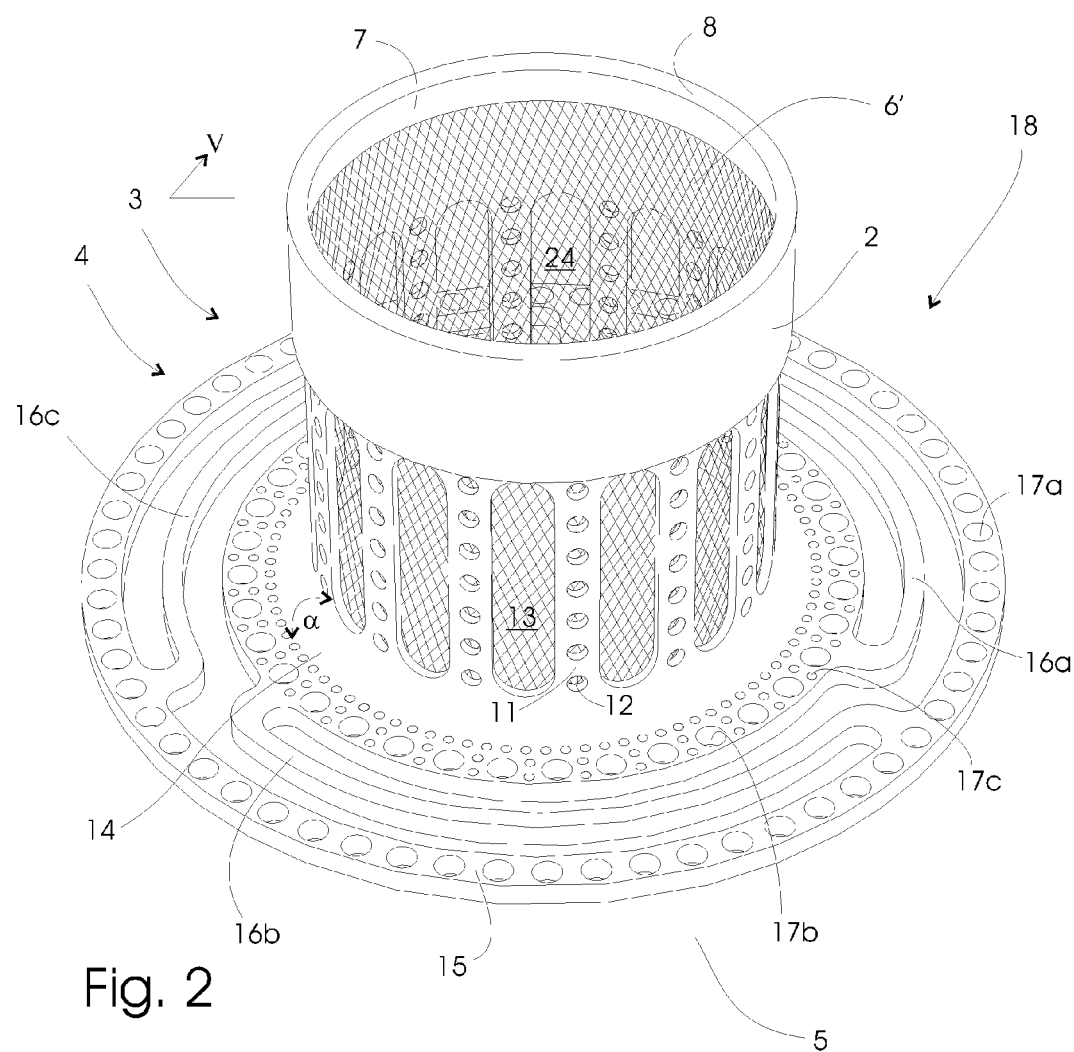
FIG. 2 shows a perspective view of a second embodiment of an implant according to the present invention.

The second embodiment 18 shown in FIG. 2 corresponds substantially to the first embodiment 1 shown in FIG. 1 and for like parts identical numerals are used. The only difference between the first 1 and the second 18 embodiment is that the ingrowth means 6' extends into intermediate section 5 down to anchoring section 5 to cover the entire internal diameter of the intermediate section 4. The annular side of the spaces or windows 13 and first connection members 11 along the internal diameter of the intermediate section 4 is covered with netting 6'. Also, in this embodiment a rim portion 7 and outer edge 8 is left free of ingrowth means.

Figure 3:
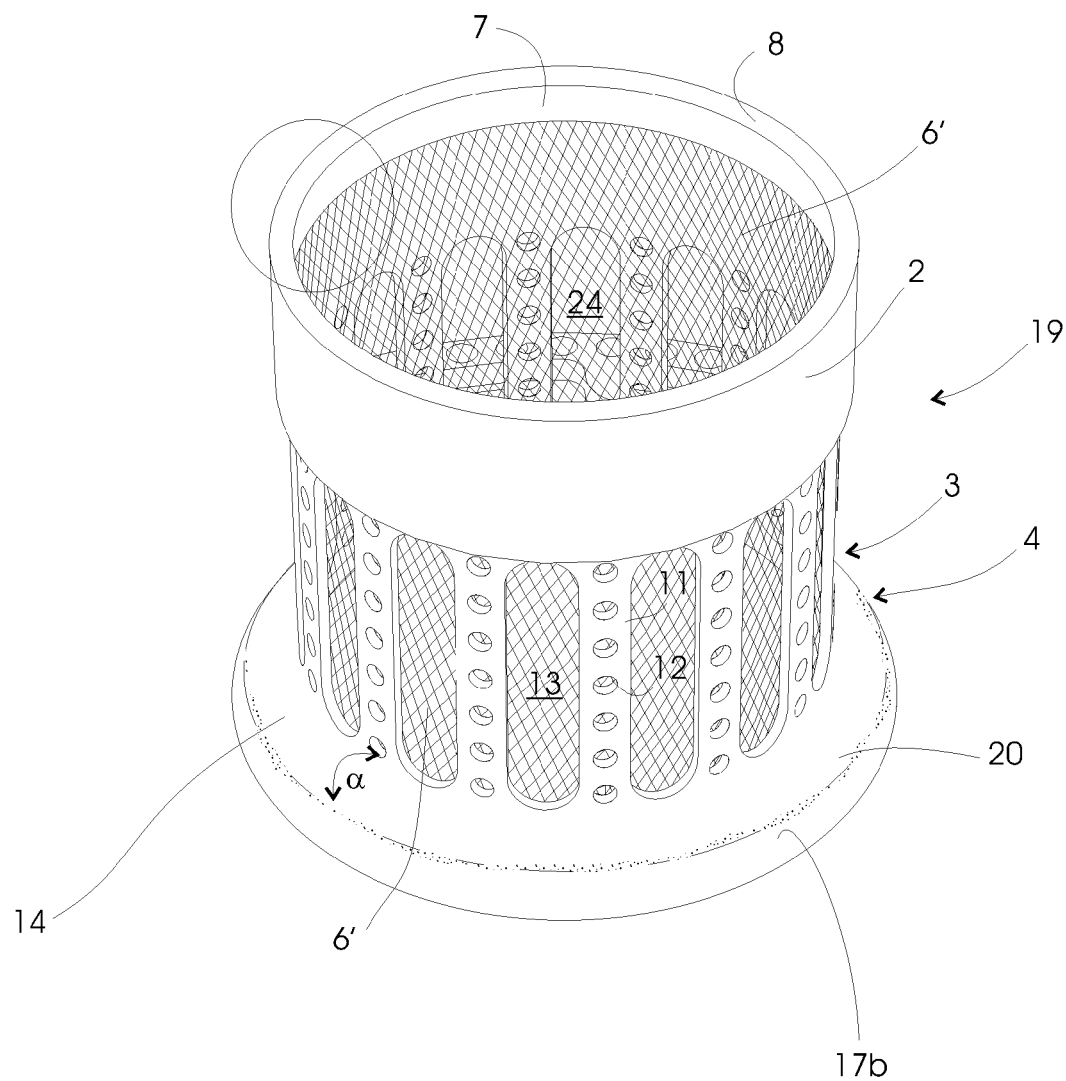
FIG. 3 shows a perspective view of a third embodiment of an implant according to the present invention.

FIG. 3 shows a third embodiment 19 of an implant according to the present invention. This embodiment 19 corresponds substantially to the second embodiment 18 shown in FIG. 2 and for like parts identical numerals are used. The only difference between the second 18 and the third 19 embodiment is that the radial extent of the anchoring section is reduced.

The anchoring section 20 of the third embodiment 19 corresponds to the inner anchoring ring 14 of the first 1 and second 18 embodiment. The anchoring section 14 has no holes, but this is optional, and holes may be provided in case needed in the actual situation, if e.g. suturing of the anchoring section is required. An adherence between the abdominal wall tissue and the serosa of the externalized body duct will be generated during healing and this adherence will secure the implant in situ against action from mechanical forces.

Figure 4:
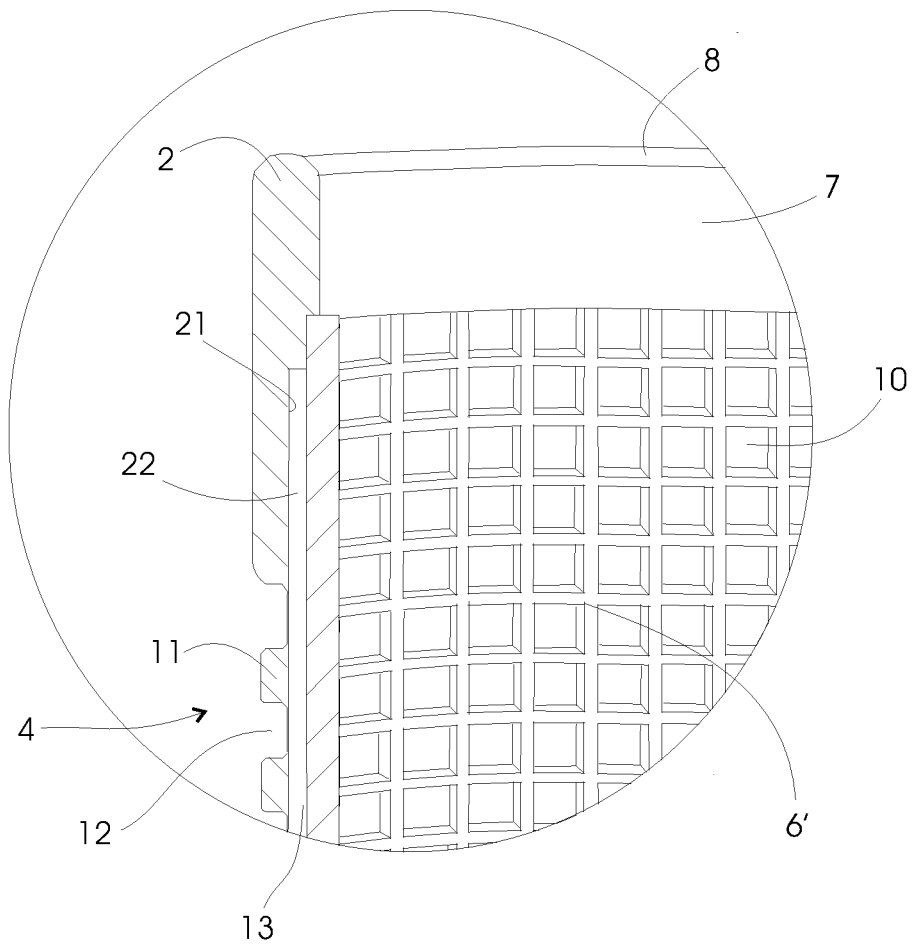
FIG. 4 shows a fragmentary, sectional view of the embodiment shown in FIG. 3.

FIG. 4 shows a detail of the embodiment shown in FIG. 3. The ingrowth means 6' extends up through the intermediate section 4 towards the rim portion 7 and outermost edge 8. Opposite the rim portion 7 adjacent the intermediate section 3 the exterior ring section 2 has a recess 21 along the internal diameter to provide a gap 22, e.g. 0.0-5.0 mm, between ingrowth means 6' and exterior ring section 2. The gap 22 serves as an escape route for new tissue and controls the direction of tissue formation during healing. New tissue formations will by way of nature be generated along the easiest route. The gap 22 provides such an easy route. New tissue formations pass via the netting 6' into the gap 22 from which the new tissue formations may find their way into the spaces 13. This route is open and unobstructed. The gap 22 is especially expedient if a stent is used for keeping the body duct in engagement with the netting 6' during healing and ingrowth. The gap 22 facilitates direction and controlling of formation of tissue away from the internal diameter and keeps the rim portion 7 free.

The new implant stoma is more flush with the exterior skin surface than conventional stomas and offers in addition a platform for attachment of pouches and caps.

The exterior ring section is shown and described in the previous figures as if the implant has no coupling and securing means for pouches or caps. However, any kind of known coupling and securing means may be used for and provided at the inventive implant. Within the scope of the present invention e.g. securing rims, and grooves can be used. Also, the exterior ring section can be configured as described in the applicant's own European Patent Application EP 04077965.4 to engage with the coupling described therein.

Figure 5:
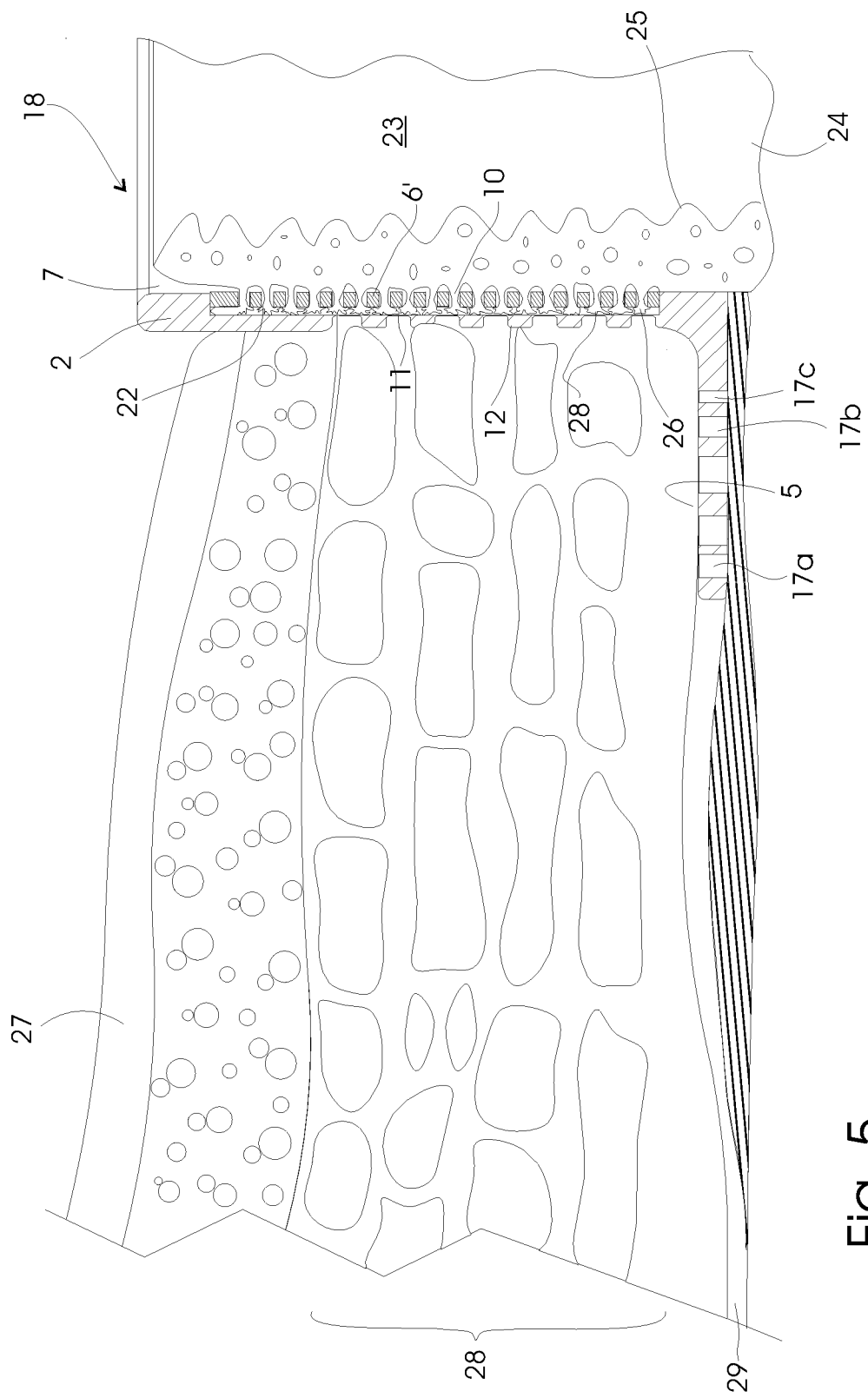
FIG. 5 shows schematically a fragmentary section of the implant of FIG. 2, taken along the line V, implanted in the abdominal wall in a first surgical mode. An intestine is externalised through the internal diameter of the implant and the ingrowth through the ingrowth means are illustrated.

FIG. 5 shows schematically a fragmentary sectional view of the implant 18 shown in FIG. 3 with an intestine 23 externalized through the internal diameter 24 using a first surgical implantation mode, and where the intestine has engaged the ingrowth means 6'. The intestinal mucosa 25 faces towards the inside of the implant 18 and the serosa 26 faces towards the ingrowth means 6' and first connection members 12. The exterior ring section 2 protrudes from the skin surface 27 and the intermediate section 4 extends though the Mm. abdominis 28 with the anchoring section 5 situated on top of the lower, deep fascia 29. As illustrated new tissue has been generated and has attached to the serosa 26 resulting in tissue infiltration of the ingrowth means 6'. Abdominal tissue 28 has invaded the transverse through-openings 12 of the first connection members 11 and a connective tissue bond between abdominal wall and intestine is indicated generated with the implant as an integrated object.

In the embodiments shown in the drawing described above the anchoring section is made as a flange extending radially from the interior section, however within the scope of the present invention the anchoring section can be modified as required. For example the anchoring can lack radially extent in which case the anchoring section extent axially a distance from the interior section and the angle α can be more than app 90° to provide conicity to the anchoring section.

Figure 6:
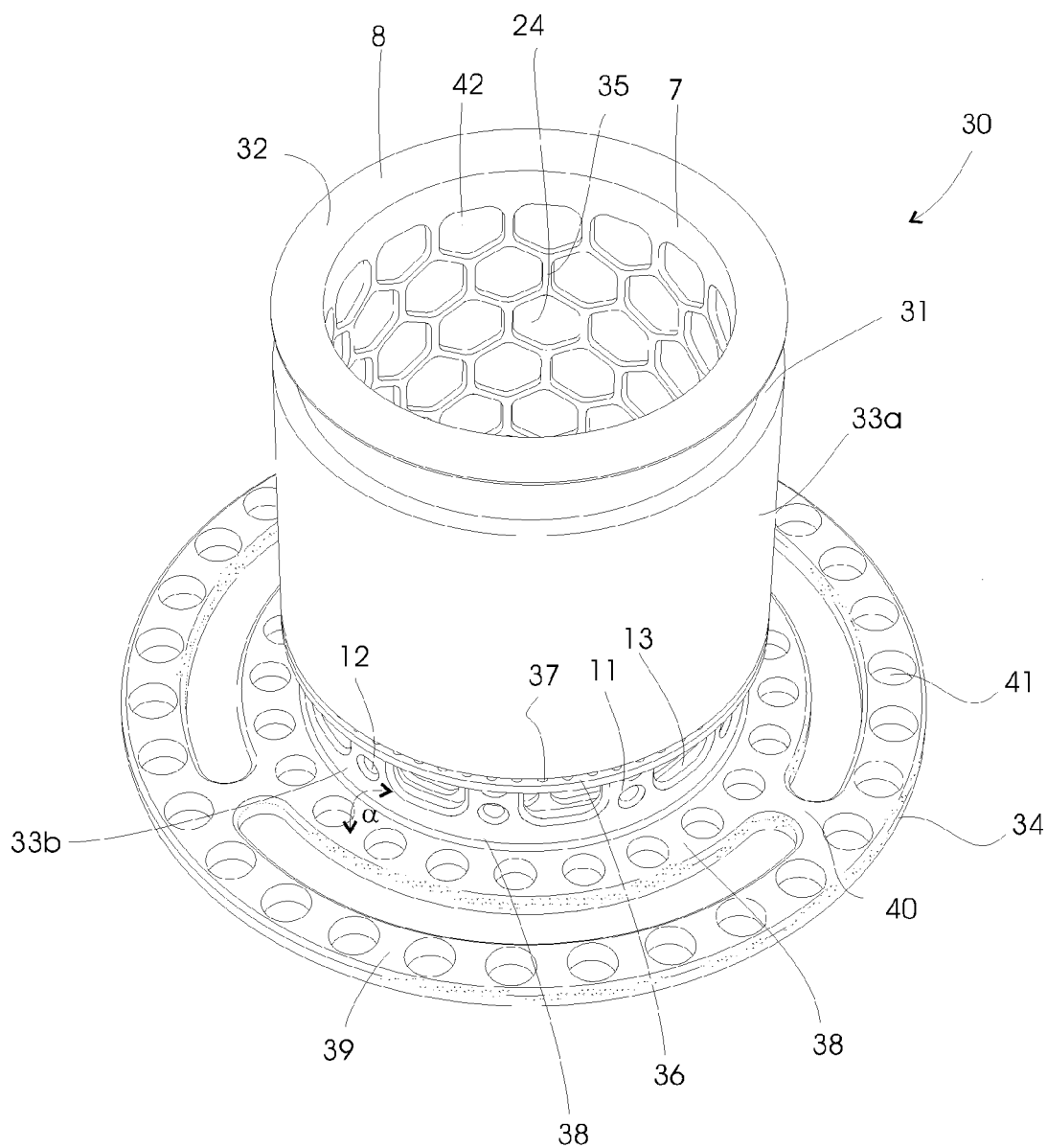
FIG. 6 shows a fourth embodiment of an implant according to the present invention.

FIG. 6 shows a fourth embodiment of an implant 30 according to the present invention. The implant 30 has an exterior ring section 31, with a coupling flange 32 for mounting of a collection bag (not shown). The exterior section 32 extends into an interior section 33 consisting of a first intermediate section part 33a, a second intermediate section part 33b and a slightly conic anchoring section 34, extending at an angle α of app. 100° from said second intermediate section part 33b. Along the inner circumference of the interior section annular ingrowth means 35 are provided in a manner similar to the manner described for the embodiments 18,19 shown in FIGS. 2 and 3, including providing a recess 21 in the exterior ring section 31 and arranging the ingrowth means 35 as disclosed in FIG. 4 to provide the gap.

The first intermediate section part 33a merges into a second intermediate section part 33b via an annular securing rib 36 having a plurality of securing holes 37 for either permanently or temporarily fastening the implant 30 during healing and ingrowth of the implant to the abdominal wall tissue. The second intermediate section part 33b is a modification of the intermediate section 4 of the first embodiment 1 of FIG. 1 in that the connection members 11 with the through-going openings 12 is much shorter. However, the second intermediate section part 33b basically serves the same function as the intermediate section 4, and for further structural description references are made to the description of FIG. 1. The anchoring section 34 has an inner anchoring ring 38 which is connected to an outer anchoring ring 39 by means of connection rods 40a, 40b, 40c. The inner and outer anchoring ring has a plurality of through holes 41, which may or may not be used for suturing or stapling or be left for tissue ingrowth.

The ingrowth means 35 are made with a plurality of laser cut hexagonal openings 42, which allows access of tissue from an externalized body duct and provide the framework for integration and fixation of the body duct to the implant.

Figure 7:
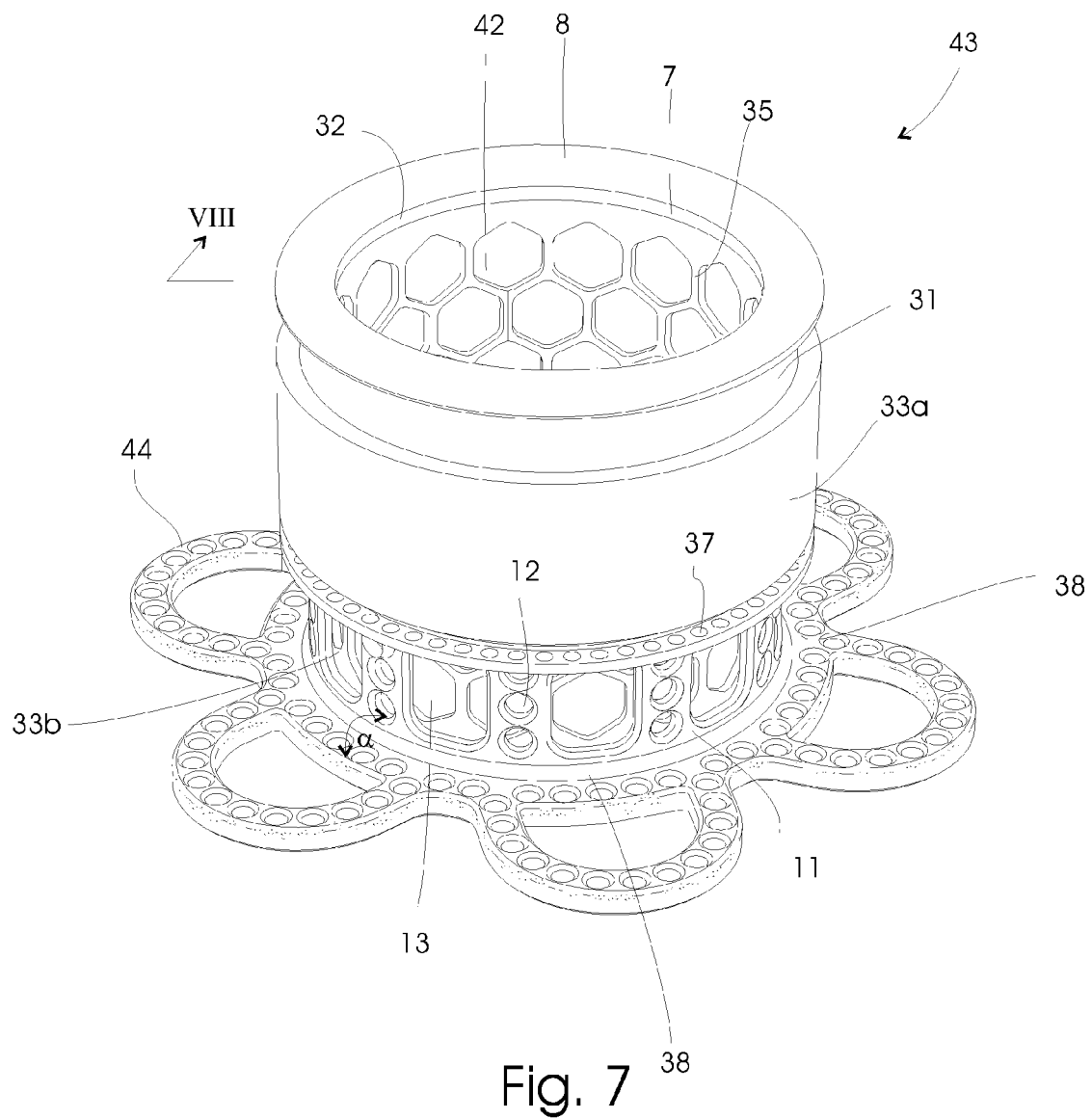
FIG. 7 shows a fifth embodiment of an implant according to the present invention.

FIG. 7 shows a fifth embodiment 43 of an implant according to the present invention. This fifth embodiment 43 is a modification of the fourth embodiment 30 shown in FIG. 6 and for like parts same reference numerals are used.

The modification consist in that the height of the first intermediate section part 33a is shortened and the height of the second intermediate section part 33b is made higher. A further modification exist in that the outer anchoring ring is composed of a plurality of semicircular segments 44 protruding as the petals on a flower from the inner anchoring ring 38. This anchoring section can be made conic or not, and may be sutured to subjacent tissue or not.

The above fifth embodiment 43 is seen in implanted state in FIG. 8 in a second surgical mode in which the inner anchoring ring 38 and the outer anchoring ring, i.e. the semicircular segments 44 is arranged below the subcutaneous fat layer on top of the upper fascia 45 without suturing to allow healing and ingrowth of connective tissue through the ingrowth means 35 and any other opening in the implant and in the gap 22. Besides from the anchoring section being situated on the upper fascia of the Mm muscularis instead of on the lower fascia 29 the second surgical mode corresponds to the first surgical mode.

The proportion between the heights of the two intermediate section parts can be modified as desired and appropriate, to comply with the patients specific needs. Conditions that may affect the choice of height are the thickness of the layers of the abdominal wall and the implantation method. If the anchoring section are to be anchored on the lower fascia as previously described for FIG. 5 a certain height is required, if however the anchoring section is situated on a tissue layer above the lower fascia the length of the interior section can be reduced.

The cross-sectional area of the channels or passageways of the ingrowth means which serves for ingrowth of connective tissue from the abdominal wall and penetration of tissue from the exterior wall of the intestine may be given any size and shape or combinations of sizes and shapes in any of the embodiments described above. For example the cross-sectional area can be made smaller along the exterior section than along the interior section in the embodiment shown in FIG. 7, and the cross-sectional area may be made oblong along the interior section and circular along the exterior section instead of purely hexagonal. Furthermore, as indicated by the dotted signature filling at the anchoring section of the fourth 30 and fifth embodiments 43 none of the implants have sharp edges.

It is emphasized that corners and edges preferably are rounded, including the corners and edges arising from the various holes in the implant, so that new tissue made during the healing and resulting interdigitation process through the holes is able to resist stress application without being lesioned, cut or otherwise damaged to thereby avoid accidental detachment, inducing of an inflammatory tissue response and internal bleedings.

Any material besides titanium which are biological acceptable, such as plastic materials, and approved for implantation can be used for the manufacture of the implant. The advantages of titanium is that it has turned out that titanium can be treated to provide the surface characteristic which is suitable for optimum fixation of the implant in the patients body.

EXAMPLES

Preclinical Investigation Study of Ingrowth in Pigs

Implantations of two embodiments of implants according to the present invention on domestic pigs were performed at Interventional Centre, Rikshospitalet, Oslo. Two domestic pigs were implanted. The experiment ended after 23 days.

Pig 1. received a modification of the embodiment shown in FIG. 3 without first connection members, and pig 2. received the embodiment shown in FIG. 1. Both implants were made of surgical grade titanium, including titanium meshes, which constitutes the ingrowth means.

The implants were placed lateral of the midline incision through the rectus muscle in the abdominal muscle layers, with the anchoring section placed on the lower inner fascia. A section of ileum was connected to the implants with the peristaltic towards the implants (reversed Roux-en-Y). In this preclinical investigation study neither the implant nor the ileum protrudes through the abdomen in order to reduce mechanical forces, prevent contamination and keep focus on the degree and quality of ingrowth.

23 days after implantation the implants and surrounding tissue were explanted and prepared for histology.

Ocular inspection showed high degree of tissue to the ingrowth means. Histological examination revealed that the mesh was adequately incorporated with connective tissue. No histological evidence of inflammation in mesh or between the ileum and the implant and the area was vascularised. The muscularis externa was continuously attached to the new connective tissue on approximately ⅔ of its circumference. The part where the mesentery was present did not reveal this good adherence.

Preclinical Investigation Study of Ingrowth in Dogs

Implantation of the implant shown in FIG. 2 were performed on two dogs at Sahlgrenska Academy, Gothenburg, Sweden. The experiment ended after 31 days.

Figure 8:
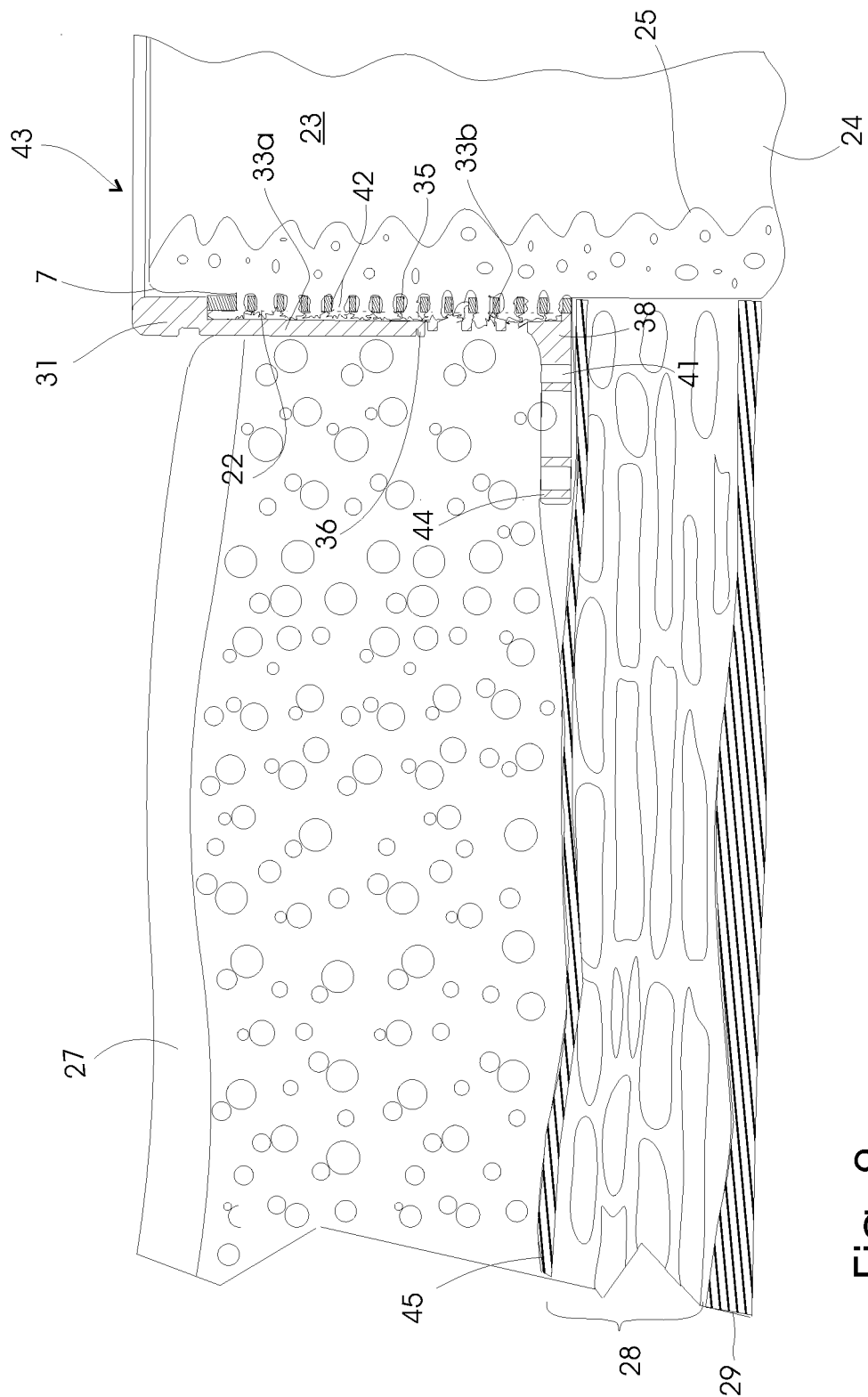
FIG. 8 shows schematically a fragmentary section of the implant of FIG. 7 taken along the line VIII, implanted in the abdominal wall in a second surgical mode. An intestine is externalised through the internal diameter of the implant and the ingrowth through the ingrowth means are illustrated.

Implants were made of commercially pure titanium and were implanted subcutaneously with the anchoring section on the upper outer fascia as shown in FIG. 8. The implant protruded through the abdominal wall. An end-to-side anastomosis was created with one branch of ileum introduced through the implant. The efferent ileum was secured by means of suturing to the peritoneum in order to prevent it from being retracted into the abdomen. The experiment ended after 31 days. Macroscopic observations during removal revealed that the upper circumference of the implant was still well above skin level and the stoma on its inside looked normal. The ileum was firmly fixated to the implant, even in the upper part. The skin was attached to the implant surface by means of fresh granulation tissue. The efferent small bowel segment heading into the abdominal aperture was of normal size and colour. The histological investigations are not yet finalized.

Manufacturing Example

The blanks of the components for the implant was cut and drilled using conventional means and technology.

The ingrowth means wad provided with passageways having hexagonal cross-sections using YAG Laser Cutting and was laser welded together with the other components of the implant to create an assembled implant structure.

The assembled titanium implant was tumbled in a Manfrid Dreher FT 4/40 VT A (Manfrid Dreher GmbH, Pforzheim, Germany) for 45 minutes using DG 6 as umbling media and S70 steel shots as compound (both obtainable from KMC Ytbehandling AB Ryttarvägen 18 B 302 60 Halmstad, Sweden). The surfaces except the surfaces of the exterior ring section was blasted using a Guyson 4171 PHASE, provided with a ceramic nozzle having a diameter of 6.4 mm. The blasting media was Alox 220 (obtainable from KMC Ytbehandling AB Ryttarvägen 18 B 302 60 Halmstad, Sweden) which was blasted at a pressure of ca. 6 bar at a distance of 150-200 mm for app. 1 minute. The resulting nominal surface finish is between Ra 0.34-0.64 μm. The surfaces was finally passivated according to ASTM F86.

The various features and structural characteristics may be combined into further advantageous embodiments within the scope of the present invention. The implants may also be pretreated with a chemical, such as an antibiotic, antifungal, or an antibacterial agent as a precautionary measure to prevent infections arising from the micro flora accidentally seeping from the body duct.

What is claimed is:

1. An implant for percutaneous implantation through the abdominal wall for encircling and engaging an externalised length of a body duct of a human or animal patient, comprising:
    an exterior ring section at least a part of which is for protruding outwardly from the abdominal wall with a free end for mounting of a detachable device, and
    an interior section for extending through the abdominal wall and inside the patient for internal fixation of the implant,
    wherein the exterior ring section and the interior section have a common axis, and
    wherein the interior section is provided with a rigid, biocompatible, integrated ingrowth means in the form of netting, mesh, maze or sponge for the ingrowth of the exterior surface of the body duct wall, whereby abdominal tissue can spread into contiguity with serosal tissue which has infiltrated the ingrowth means.

2. The implant according to claim 1, wherein the interior section comprises an intermediate section emerging from the exterior ring section, wherein the intermediate section is optionally axially divided into a first intermediate section part and a second intermediate section part emerging from the first intermediate section part, the interior section extends into an anchoring section, one of the second intermediate section part or intermediate section comprises circumferentially spaced apart first connection members connecting the second intermediate section part or the intermediate section with the anchoring section.

3. The implant according to claim 2, wherein the entire internal circumference of any of the intermediate section or the intermediate section parts is provided with integrated ingrowth means for the exterior surface of the body duct wall.

4. The implant according to claim 1, wherein the integrated ingrowth means has a plurality of passageways or channels that provide for ingrowth of the serosa of the exterior surface of the body duct wall.

5. The implant according to claim 4, wherein any of the plurality of passageways or channels or openings have a polygonal cross-section.

6. The implant according to claim 2, wherein the anchoring section extends radially from the intermediate section or the second intermediate section part opposite the exterior ring section.

7. The implant according to claim 6, wherein the anchoring section is conic.

8. The implant according to claim 2, wherein the anchoring section comprises an inner anchoring ring extending from the intermediate section or the second intermediate section part, an outer anchoring ring, and at least one second connection member for connecting the inner anchoring ring with the outer anchoring ring.

9. The implant according to claim 2, wherein the implant is modified so that any or both of the intermediate sections are made entirely as integrated ingrowth means.

10. The implant according to claim 1, wherein a radial thickness of the ingrowth means is equal to or smaller than the wall thickness of the body duct.

11. The implant of claim 1, wherein the internal circumference of at least a part of the exterior ring section above the interior section is also provided with integrated ingrowth means.

12. The implant of claim 11, wherein the interior section comprises an intermediate section extending into an anchoring section.

13. The implant of claim 12, wherein the intermediate section comprises circumferentially spaced apart first connection members arranged to connect the exterior ring section with the anchoring section.

14. The implant of claim 12, wherein the integrated ingrowth means extends into the intermediate section down to the anchoring section.

15. The implant of claim 1 in combination with a detachable device for mounting on the exterior ring section.

16. The implant of claim 1 in combination with a bag for mounting on the implant.

17. The implant of claim 11, wherein the integrated ingrowth means of the exterior ring section part extends into the interior section.

18. The implant of claim 11, wherein the integrated ingrowth means of the exterior ring section part is in the form of netting, mesh, maze or sponge.

19. The implant of claim 11, wherein the integrated ingrowth means of the exterior ring section part is provided in the exterior ring section only at the internal circumference thereof.

20. The implant of claim 11, wherein the integrated ingrowth means of the exterior ring section part is rigid.

21. The implant of claim 11, wherein the integrated ingrowth means of the exterior ring section part is in the form of a maze or sponge.

22. The implant of claim 1, wherein the integrated ingrowth means is in the form of a mesh.

23. The implant of claim 22, wherein the mesh comprises openings with a hexagonal cross-section.

24. The implant of claim 1, wherein the interior section comprises an intermediate section emerging from the exterior ring section, and the interior section extends into an anchoring section.

25. The implant of claim 24, wherein the anchoring section is conic.

26. The implant of claim 24, wherein the anchoring section comprises an inner anchoring ring connected to an outer anchoring ring.

27. The implant of claim 26, wherein the anchoring section comprises at least one connection member for connecting the inner anchoring ring with the outer anchoring ring.

28. The implant of claim 26, wherein the outer anchoring ring has a greater diameter than the inner anchoring ring and is concentric with the inner anchoring ring.

29. The implant of claim 24, wherein the anchoring section is annular.

30. The implant of claim 24, wherein the anchoring section comprises a flange extending radially from the interior section.

31. The implant of claim 9, wherein the integrated ingrowth means is in the form of a mesh.

32. An implant for percutaneous implantation through the abdominal wall for encircling and engaging an externalized length of a body duct of a human or animal patient, comprising:
    an exterior ring section at least a part of which is for protruding outwardly from the abdominal wall with a free end for mounting of a detachable device, and
    an interior section for extending through the abdominal wall and inside the patient for internal fixation of the implant,
        wherein the exterior ring section and the interior section have a common axis, and
        wherein the internal circumference of at least a part of the exterior ring section above the interior section is provided with a rigid, biocompatible, integrated ingrowth means in the form of netting, mesh, maze or sponge for the ingrowth of the exterior surface of the body duct wall.

33. The implant of claim 32, wherein the integrated ingrowth means is provided in the exterior ring section only at the internal circumference thereof.

34. The implant of claim 32, wherein the integrated ingrowth means is in the form of a maze or sponge.

\* \* \* \* \*

UNITED STATES PATENT AND TRADEMARK OFFICE
CERTIFICATE OF CORRECTION

PATENT NO. : 8,647,304 B2
APPLICATION NO. : 12/280610
DATED : February 11, 2014
INVENTOR(S) : Axelsson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 916 days.

Signed and Sealed this
Twenty-ninth Day of September, 2015

Michelle K. Lee
*Director of the United States Patent and Trademark Office*